(12) United States Patent
Howard

(10) Patent No.: US 11,633,121 B2
(45) Date of Patent: Apr. 25, 2023

(54) ABLATION CHECK PULSE ROUTINE AND INTEGRATION FOR ELECTROPORATION

(71) Applicant: Medtronic, Inc., Minneapolis, MN (US)

(72) Inventor: Brian T. Howard, Hugo, MN (US)

(73) Assignee: Medtronic, Inc., Minneapolis, MN (US)

( * ) Notice: Subject to any disclaimer, the term of this patent is extended or adjusted under 35 U.S.C. 154(b) by 461 days.

(21) Appl. No.: 15/669,048

(22) Filed: Aug. 4, 2017

(65) Prior Publication Data

US 2019/0038171 A1    Feb. 7, 2019

(51) Int. Cl.
*A61B 5/05*    (2021.01)
*A61B 18/14*    (2006.01)
(Continued)

(52) U.S. Cl.
CPC .................. *A61B 5/05* (2013.01); *A61B 5/24* (2021.01); *A61B 5/7275* (2013.01);
(Continued)

(58) Field of Classification Search
CPC ..... A61B 5/05; A61B 5/04001; A61B 5/7275; A61B 18/1492; A61B 2018/0016; A61B 2018/00214; A61B 2018/00351; A61B 2018/00577; A61B 2018/00613; A61B 2018/00642; A61B 2018/00702; A61B 2018/00738; A61B 2018/00767; A61B 2018/00839; A61B 2018/0212;
(Continued)

(56) References Cited

U.S. PATENT DOCUMENTS

| 4,712,558 A | 12/1987 | Kidd et al. |
| 6,023,638 A | 2/2000 | Swanson |

(Continued)

OTHER PUBLICATIONS

Thorsten Stroh et al., Combined Pulse Electroporation—A Novel Strategy for Highly Efficient Transfection of Human and Mouse Cells, Published: Mar. 2, 2010, https://doi.org/10.1371/journal.pone.0009488, 10 pages.

(Continued)

*Primary Examiner* — Ronald Hupczey, Jr.
*Assistant Examiner* — Bradford C. Blaise
(74) *Attorney, Agent, or Firm* — Michael Best & Friedrich LLP

(57) ABSTRACT

Devices, systems, and methods relating to a low-voltage, pre-treatment pulse routine for evaluating a potential for non-target tissue damage from the delivery of energy, such as electroporation energy to an area of target tissue. In one embodiment, a medical system includes a medical device having a treatment element; and a control unit in communication with the medical device, the control unit being configured to: deliver a low-voltage, pre-treatment pulse routine through the treatment element to an area of target tissue; determine whether the low-voltage, pre-treatment pulse routine has a stimulation effect on an area of non-target tissue; and deliver an ablation energy routine through the treatment element to the area of target tissue when the control unit determines that the low-voltage, pre-treatment pulse routine does not have a stimulation effect on the area of non-target tissue.

19 Claims, 10 Drawing Sheets

(51) Int. Cl.
*A61N 1/36* (2006.01)
*A61B 5/24* (2021.01)
*A61B 5/00* (2006.01)
*A61B 18/00* (2006.01)
*A61B 18/02* (2006.01)
*A61N 7/02* (2006.01)

(52) U.S. Cl.
CPC ............ *A61B 18/1492* (2013.01); *A61N 1/36* (2013.01); *A61B 2018/0016* (2013.01); *A61B 2018/00214* (2013.01); *A61B 2018/00351* (2013.01); *A61B 2018/00577* (2013.01); *A61B 2018/00613* (2013.01); *A61B 2018/00642* (2013.01); *A61B 2018/00702* (2013.01); *A61B 2018/00738* (2013.01); *A61B 2018/00767* (2013.01); *A61B 2018/00839* (2013.01); *A61B 2018/0212* (2013.01); *A61B 2018/144* (2013.01); *A61B 2560/0223* (2013.01); *A61N 7/022* (2013.01)

(58) Field of Classification Search
CPC ...... A61B 2018/144; A61B 2560/0223; A61B 5/0492; A61N 1/36; A61N 7/022
See application file for complete search history.

(56) References Cited

U.S. PATENT DOCUMENTS

| | | | |
|---|---|---|---|
| 6,428,537 B1* | 8/2002 | Swanson | A61B 18/1492 606/41 |
| 6,618,626 B2* | 9/2003 | West, Jr. | A61B 18/148 606/34 |
| 6,780,178 B2 | 8/2004 | Palanker et al. | |
| 6,821,274 B2 | 11/2004 | McHale et al. | |
| 9,872,989 B2* | 1/2018 | Jung | A61N 1/3601 |
| 2008/0045946 A1 | 2/2008 | Vaska | |
| 2010/0228246 A1* | 9/2010 | Marion | A61B 18/1206 606/37 |
| 2010/0262042 A1 | 10/2010 | Kim | |
| 2011/0004264 A1* | 1/2011 | Siejko | A61N 1/371 607/28 |
| 2011/0098761 A1 | 4/2011 | Wittenberger et al. | |
| 2011/0275952 A1* | 11/2011 | Johnson | A61B 18/1233 600/547 |
| 2013/0109994 A1* | 5/2013 | Cho | A61B 5/1104 600/534 |
| 2014/0358135 A1* | 12/2014 | Sambelashvili | A61B 5/7282 606/34 |
| 2015/0126922 A1* | 5/2015 | Willis | A61N 1/327 604/21 |
| 2015/0202448 A1* | 7/2015 | Hoffer | A61N 1/0551 607/42 |

OTHER PUBLICATIONS

International Search Report and Written Opinion dated Sep. 19, 2018, for corresponding International Application No. PCT/US2018/039407; International Filing Date: Jun. 26, 2018 consisting of 12-pages.

* cited by examiner

ABLATION CHECK PULSE ROUTINE AND INTEGRATION FOR ELECTROPORATION

TECHNICAL FIELD

The devices, systems, and methods described herein relate to a low-voltage, pre-treatment pulse routine for evaluating a potential for non-target tissue damage from the delivery of energy, such as electroporation energy to an area of target tissue.

BACKGROUND

When treating particular regions of tissue, through thermal energy interaction or the like for example, it may be difficult to direct or control the depth and intensity of the heat transfer. The delivery of thermal energy or other therapeutic modality, such as radiofrequency or cryogenic applications, may not necessarily be contained to the exact region or depth desired for treatment, as the tissue may have varying therapy-conducive properties affected by the surrounding physiological environment. Failure to limit thermal treatment or exposure to just the target tissue may otherwise negatively and adversely affect surrounding tissue structures or organs that are sensitive and susceptible to undesired damage.

For example, when attempting to treat cardiac tissue, sensitive tissue structures abound that may react adversely to thermal applications. In particular, when thermally treating or ablating tissue in or about the heart, it is essential that critical physiological structures such as the phrenic nerves are not inadvertently destroyed during such ablation therapy. Phrenic nerve injury (PNI) is a well-known risk of cardiac ablations which can have severe consequences because of the phrenic nerve's key functions and a common risk because of the nerve's anatomical locations and an inability to more accurately assess an ablative therapy's proximity to the nerve. The phrenic nerve is made up mostly of motor nerve fibers that produce contractions of the diaphragm and thus affect breathing and respiration patterns and conditions. In addition, the phrenic nerve provides sensory innervation for many components of the mediastinum and pleura, as well as the upper abdomen, especially the liver, and the gall bladder.

The right and left phrenic nerves both run in very close proximity to the heart. Both phrenic nerves run from C3, C4 and C5 vertebrae along the anterior scalene muscle deep to the carotid sheath. The right phrenic nerve passes over the brachlocephalic artery, posterior to the subclavian vein, and then crosses the root of the right lung anteriorly and then leaves the thorax by passing through the vena cava hiatus opening in the diaphragm at the level of T8. The right phrenic nerve passes over the right atrium. The left phrenic nerve passes over the pericardium of the left ventricle and pierces the diaphragm separately.

The phrenic nerve segments in normal anatomy are located in close proximity to the right atrium, left atrium, and left ventricle, which cardiac regions may be the location or origin of heart arrhythmias or other physiological maladies and thus targeted for tissue ablation in order to remove or otherwise remedy the abnormal electrophysiological occurrence. In thermally treating or ablating select cardiac regions, the phrenic nerve may be at risk of being similarly, although unintentionally, ablated. This could severely impact the normal respiratory functioning of the patient. Such injury can manifest as a transient phrenic functional block, transient phrenic nerve palsy (PNP), or longer-term phrenic nerve injury (PNI). These injuries reduce respiratory function and can require many weeks or months to resolve. In the worst cases, this reduced function requires mechanical ventilation assistance to maintain respiration. As such, the risk of such unintentional and undesirable destruction or application of thermal energy to this and other cursory structures compels a desire to monitor or otherwise detect potentially-damaging consequences during treatment.

A currently used method of determining risk to the phrenic nerve or other sensitive structures prior to ablation involves establishing the ability of an ablation device to cause stimulation of the diaphragm through activating the phrenic nerves with every single placement of the ablation device. Not only does this method use what are currently very limited pacing routines meant for cardiac pacing, but the method is also time consuming and non-specific to the treatment or injury potential. As a result, additional monitoring is still required during thermal ablation procedures. Of particular concern, however, are new, comparatively fast ablation modalities such as electroporation which, depending on a particular implementation, may not even allow the time necessary for such assessments, thus making the determination of therapeutic risk prior to treatment even more important. Additionally, the rapidity of such ablation modalities is greatly hindered when subject to the established process, which incorporates multiple systems with each placement to achieve the most basic indication of sensitive structure proximity.

Such standard monitoring technique used during an ablation is typically performed using one of two methods using continuous pacing of the phrenic nerve: 1) using continuous fluoroscopy during the ablation to visualize a consistent diaphragmatic response; or 2) palpation of the abdomen to confirm diaphragmatic movement. Both methods require vigilance on the part of the operator, and can distract the physician from the main focus of the diagnostic or treatment procedure at hand. Further, in the case of fluoroscopic monitoring, the patient is exposed to increased x-ray radiation. Such monitoring is the currently accepted practice and is useful because of the potentially slow mechanism of PNI induced by thermal ablation methods.

Further, although these methods may be used to detect potential effects on the phrenic nerve when using treatment energy modalities such as radiofrequency (RF) energy delivery and cryogenic treatment, it is not well established how to detect the potentially dangerous ablation zone for the phrenic nerve, or other nerve or muscle non-target tissues, when delivering pulsed-field energy and/or irreversible electroporation energy. Such an energy modality is being used with increasing frequency because it is less likely to cause side effects common to RF or cryotreatment, such as stenosis and fistulas.

Additionally, there are other such innervations or active muscle groups that may be identified throughout the body for other such ablation injury mitigations. Further, stimulation ahead of ablations using any energy modality, such as for purposes of treating cancers, may be beneficial.

SUMMARY

The devices, systems, and methods described herein relate to a low-voltage, pre-treatment pulse routine for evaluating a potential for non-target tissue damage from the delivery of energy, such as electroporation energy to an area of target tissue. In one embodiment, a medical system includes a medical device having a treatment element; and a control unit in communication with the medical device, the control unit being configured to: deliver a low-voltage, pre-treatment pulse routine through the treatment element to an area of target tissue, the low-voltage, pre-treatment pulse routine being configured to have a stimulation effect within an area of non-target tissue when the non-target tissue is within a predetermined distance from the area of target tissue and to not have a stimulation effect within the area of non-target tissue when the area of non-target tissue is outside of the predetermined distance from the area of target tissue; and deliver an ablation energy routine through the treatment element to the area of target tissue when the low-voltage, pre-treatment pulse routine does not have a stimulation effect on the area of non-target tissue.

In one aspect of the embodiment, delivery of the ablation energy routine includes the use of at least one of irreversible electroporation, radiofrequency ablation, cryoablation, and high intensity focused ultrasound.

In one aspect of the embodiment, the system further includes a stimulation monitoring device in communication with the control unit. In one aspect of the embodiment, the stimulation monitoring device includes at least one of an accelerometer and an electromyography device.

In one aspect of the embodiment, the control unit is configured to determine whether the low-voltage, pre-treatment pulse routine has a stimulation effect on an area of non-target tissue based on signals received by the control unit from the stimulation monitoring device.

In one aspect of the embodiment, the control unit is further configured to select the low-voltage, pre-treatment pulse routine based on the ablation energy routine and adjust the ablation energy routine when the low-voltage, pre-treatment pulse routine has a stimulation effect on the area of non-target tissue.

In one aspect of the embodiment, the control unit is further configured to automatically adjust at least one of voltage and pulse width of the ablation energy routine before an initiation of the ablation energy routine based on the determination of the maximum stimulation distance from the treatment element.

In one aspect of the embodiment, the low-voltage, pre-treatment pulse routine includes the delivery of energy having a voltage between 0.1 V and 100 V.

In one aspect of the embodiment, the low-voltage, pre-treatment pulse routine includes the delivery of energy having a voltage of 40 V and a pulse width of 10 µs.

In one aspect of the embodiment, the low-voltage, pre-treatment pulse routine includes the delivery of a monophasic pulse.

In one aspect of the embodiment, the low-voltage, pre-treatment pulse routine includes the delivery of a plurality of monophasic pulses.

In one aspect of the embodiment, the low-voltage, pre-treatment pulse routine includes the delivery of at least one biphasic pulse.

In one aspect of the embodiment, the low-voltage, pre-treatment pulse routine includes the delivery of at least one pulse having a sinusoidal waveform.

In one aspect of the embodiment, the control unit includes a user input device for at least one of a user selection of the low-voltage, pre-treatment pulse routine and a user initiation of the low-voltage, pre-treatment pulse routine.

In one aspect of the embodiment, the control unit is further configured to automatically deliver the ablation energy routine through the plurality of electrodes to the area of target tissue when the control unit determines that the low-voltage, pre-treatment pulse routine does not have a stimulation effect on the area of non-target tissue.

In one aspect of the embodiment, the control unit is further configured to accept a user input for an initiation of the delivery of the ablation energy routine through the plurality of electrodes to the area of target tissue when the user determines that the low-voltage, pre-treatment pulse routine does not have a stimulation effect on the area of non-target tissue.

In one embodiment, a medical system includes: a medical device having a treatment element with a plurality of electrodes; a stimulation monitoring device; and a control unit in communication with the medical device and the stimulation monitoring device, the control unit including an ablation energy source and being configured to: determine an ablation energy routine; determine a low-voltage, pre-treatment pulse routine based on the ablation energy routine, the low-voltage, pre-treatment pulse routine including the delivery of energy having a voltage between 0.1 V and 100 V; deliver the low-voltage, pre-treatment pulse routine through the treatment element to an area of target tissue; determine whether the low-voltage, pre-treatment pulse routine has a stimulation effect on an area of non-target tissue; automatically adjust at least one of voltage and pulse width of the ablation energy routine before an initiation of a delivery of the ablation energy to the area of target tissue based on a determination that the low-voltage, pre-treatment pulse routine has a stimulation effect on the area of non-target tissue; and deliver ablation energy through the treatment element to the area of target tissue.

In one aspect of the embodiment, the low-voltage, pre-treatment pulse routine includes the delivery of energy having a pulse width of 10 µs.

In one embodiment, a method of irreversibly electroporating an area of target tissue without adversely affecting an area of non-target tissue includes: delivering a low-voltage, pre-treatment pulse routine through a treatment element of a medical device to an area of target tissue, the low-voltage, pre-treatment pulse routine including the delivery of energy having a voltage between 0.1 V and 100 V; determining whether the low-voltage, pre-treatment pulse routine has an adverse effect on an area of non-target tissue; when it is determined that the low-voltage, pre-treatment pulse routine has a stimulation effect on the area of non-target tissue, adjusting at least one ablation parameter of an electroporation energy routine before an initiation of electroporation energy delivery to the area of target tissue such that the electroporation energy delivery to the area of target tissue would not have an adverse effect on the area of non-target tissue; and then delivering electroporation energy through the treatment element to the area of target tissue.

In one aspect of the embodiment, the at least one ablation parameter of the electroporation energy routine includes at least one of voltage, number of pulses, number of applications, and pulse width.

In one aspect of the embodiment, the determining whether the low-voltage, pre-treatment pulse routine has an adverse effect on an area of non-target tissue is based at least in part on signals received from a stimulation monitoring device.

DETAILED DESCRIPTION

Figure 1:
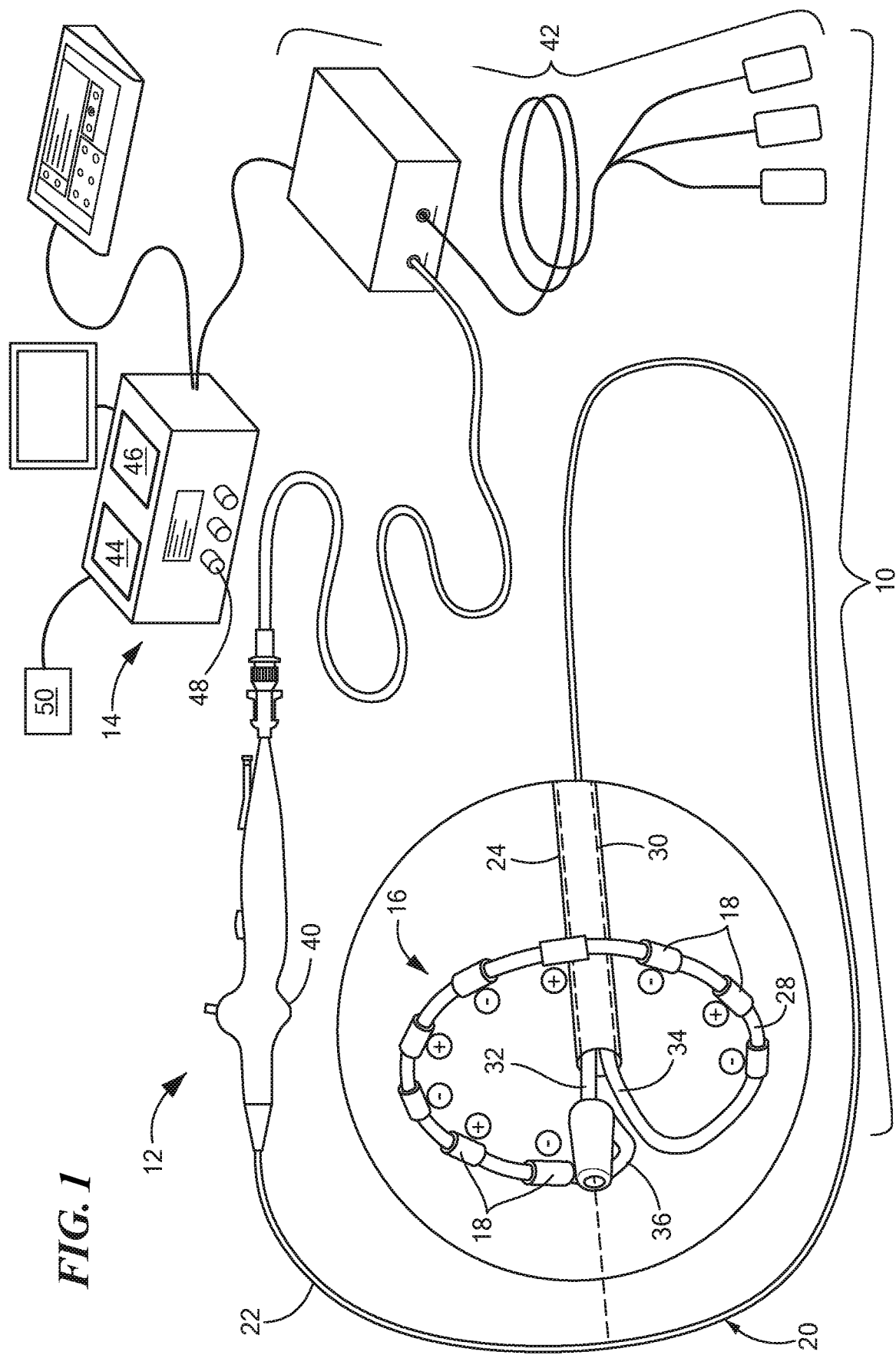
FIG. 1 shows an exemplary medical system for delivering a low-voltage, pre-treatment pulse routine and treatment or ablation energy.

The devices, systems, and methods described herein relate to a pre-treatment (or pre-ablation) pulse routine for evaluating a potential for non-target tissue damage from the delivery of energy, such as electroporation energy to an area of target tissue. This pre-treatment pulse routine may also be referred to as a pre-treatment or pre-ablation check routine. The tissue area affected by a particular treatment may be determined by the delivery parameters, as different delivery parameters may require different pulse test routines to appropriately cause an effect in the tissue area treated with use of those parameters. That is, each ablation setting, mode, device, tissue target, and/or the like may necessitate unique test pulse matters to test the correct area of the treatment's effect. Before describing in detail exemplary embodiments, it is noted the system and method components have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

As used herein, relational terms, such as "first," "second," "top" and "bottom," and the like, may be used solely to distinguish one entity or element from another entity or element without necessarily requiring or implying any physical or logical relationship or order between such entities or elements. The terminology used herein is for the purpose of describing particular embodiments only and is not intended to be limiting of the concepts described herein. As used herein, the singular forms "a", "an" and "the" are intended to include the plural forms as well, unless the context clearly indicates otherwise. It will be further understood that the terms "comprises," "comprising," "includes" and/or "including" when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

In embodiments described herein, the joining term, "in communication with" and the like, may be used to indicate electrical or data communication, which may be accomplished by physical contact, induction, electromagnetic radiation, radio signaling, infrared signaling or optical signaling, for example. One having ordinary skill in the art will appreciate that multiple components may interoperate and modifications and variations are possible of achieving the electrical and data communication.

Referring now to FIG. 1, a medical system is shown and is generally designated as '10'. The medical system 10 may include a medical device 12 and a control unit 14 in communication with the medical device 12. The medical device 12 may be configured to deliver energy (for example, pulsed-field ablation (PFA) and/or electroporation energy) for treating or ablating an area of target tissue and also configured to deliver a pre-treatment pulse routine to evaluate a potential for non-target tissue damage from the delivery of energy.

In one embodiment, the medical device 12 may be a catheter that includes one or more treatment elements 16 for energetic or other therapeutic interaction between the device and a treatment site. The treatment element(s) 16 may include one or more electrodes 18. The electrode(s) 18 may deliver, for example, pulsed-field ablation energy, electroporation energy, and/or other energetic transfer with a tissue area in proximity to the area of target tissue, such as cardiac tissue.

The medical device 12 may include an elongate body 20 passable through a patient's vasculature and/or positionable proximate to an area of target tissue for diagnosis or treatment, such as a catheter, sheath, or intravascular introducer. The elongate body 20 may define a proximal portion 22 and a distal portion 24, and may further include one or more lumens disposed within the elongate body 20 that provide mechanical, electrical, and/or fluid communication between the proximal portion 22 of the elongate body 20 and the distal portion 24 of the elongate body 20, which may include the treatment element(s) 16. In one embodiment, the elongate body distal portion 24 may include a treatment element 16 having a carrier arm 28 to which plurality of electrodes 18 are affixed. The treatment element 16 and/or elongate body distal portion 24 may be transitionable between a linear, or at least substantially linear, first configuration and a hooped, circular, or arcuate, or at least substantially hooped, circular, or arcuate, second configuration. The device 12 may include a central or guidewire lumen 30 within which a shaft 32 may be at least partially located. In one embodiment, the carrier arm 28 may have a proximal end 34 that is coupled to the elongate body distal portion 24 and a distal end 36 that is coupled to a distal portion of the shaft 32. The shaft 32 may be longitudinally slidable or movable within the guidewire lumen 30, and longitudinal movement of the shaft 32 may cause the treatment element 16 to transition between the first and second configurations.

Referring again to FIG. 1, the medical device 12 may include a handle 40 coupled to the elongate body proximal portion 22. The handle 40 may include circuitry for identification and/or use in controlling of the medical device 12 or another component of the system 10. Additionally, the handle 40 may also include connectors that are mateable to the control unit 14 to establish communication between the medical device 12 and one or more components or portions of the control unit 14. The handle 40 may also include one or more actuation or control features that allow a user to control, deflect, steer, or otherwise manipulate a distal portion of the medical device 12 from the proximal portion of the medical device 12. For example, the handle 40 may include one or more components such as a lever or knob for manipulating the elongate body 20 and/or additional components of the medical device 12.

The system 10 may further include a navigation system 42 and/or other system components for performing a particular medical procedure. The medical device 12 may be coupled directly to the control unit 14 or may be indirectly coupled to the control unit 14 through the navigation system 42 or other intermediate system component (for example, as shown in FIG. 1).

As used herein, the term "control unit 14" for simplicity may include any system components that are not part of the medical device 12 itself, other than components of the navigation system 16 and the imaging system (if included), regardless of whether the component is physically located within or external to the control unit 14. Further, the navigation system 42 may be a standalone system in communication with the control unit 14 or may be contained within or integrated with the control unit 14, even though it is shown as being physically separated from the control unit in FIG. 1. The control unit 14 may include one or more components for the delivery of one or more energy modalities for which the system is used. For example, the control 14 unit may include an energy source 44 as a treatment or diagnostic mechanism in communication with the treatment element(s) 16 of the device 12. As a non-limiting example, the energy source 44 may be an pulsed-field ablation and/or electroporation energy generator having a plurality of output channels and operable in one or more modes of operation (for example, unipolar mode and/or bipolar mode) and or may be configured to deliver electrical energy, such as both high-voltage energy and low-voltage energy.

The control unit 14 may include one or more controllers, processors, and/or software modules containing instructions or algorithms to provide for the automated operation and performance of the features, sequences, or procedures described herein. For example, the control unit 14 may include processing circuitry 46 with a memory and a processor. The memory may be in electrical communication with the processor and may have instructions that, when executed by the processor, configure the processor to receive, process, or otherwise use signals from the device 12. Further, the control unit 14 may include one or more use input devices, controllers, and displays for collecting and conveying information from and to the user.

The system 10 may further provide for the stimulation, measuring and/or monitoring of a physiological condition of a patient, as well as subsequent triggering or actuation of one or more predetermined, automated protocols or procedures in response to the monitored/measured condition. For example, the processing circuitry 46 may be configured to execute a pre-treatment pulse routine before the delivery of ablation or treatment energy. The control unit 14 may include a dedicated user input device 48 (for example, a button, switch, touch-screen menu, or the like) that allows the user to quickly and easily execute the pre-treatment pulse routine before initiating a delivery of treatment or ablation energy. A pre-treatment pulse routine may be more or less conservative for determining proximity to an area of non-target tissue, based on variables such as system parameters, medical device used, target tissue type, non-target tissue type, energy modality of the intended therapy, user's assessment/judgment, or the like. In a non-limiting example, the pre-treatment pulse routine may include the delivery of one or more biphasic, bipolar pulses for which the pulse width of each phase is 10 μs with an amplitude of 40 V. However, it will be understood that different pulse widths and/or voltages may be used, as is discussed in greater detail below. The system 10 may include one or more stimulation monitoring devices 50, such as diaphragmatic or thoracic excursion assessment devices (for example, accelerometers that may be placed on the patient's skin proximate the diaphragm) that may be used to detect diaphragmatic or thoracic movement as a result of phrenic nerve stimulation. These stimulation monitoring device(s) 50 may be in wireless or wired communication with the control unit processing circuitry 46, and may provide information to the processing circuitry 46 about movement of the diaphragm and thoracic cavity in one or more planes. In one embodiment, a 3-axis accelerometer may be used. The implemented accelerometer(s) may operate according to any of a number of sensing methodologies, such as measuring the displacement of a suspended proof mass; measuring piezoresistive effects from movement of a proof mass; and/or by measuring differential capacitive changes by attaching a proof mass to a capacitive plate, for example. The accelerometers may be positioned on or about an external surface of the diaphragm and/or thoracic cavity such that they are operable to detect diaphragmatic movement. The system 10 may optionally include a secondary device, such as an assessment device (not shown), having one or more sensors that may be used to monitor or record electromyography ("EMG") measurements of the diaphragm and/or thoracic musculature. An electromyograph detects the electrical potential generated by muscle cells when these cells are both mechanically active and at rest. To perform intramuscular EMG, an electrode may be inserted through the skin into the muscle tissue. Subsequently, electrical signals may be taken upon contraction of the muscle (such as in response to the induced excitation of the targeted tissue structure) and again during relaxation. The shape, size and frequency of the resulting muscle motor unit potentials can then be analyzed to establish a baseline or threshold value for later comparison. In cases where intramuscular EMG may be considered too invasive or unnecessary, a surface electrode may be used to monitor the muscle activation. Additionally or alternatively, stimulation may be detected visually or manually by the physician, such as through palpation of the abdomen to confirm diaphragmatic movement. As discussed above, the phrenic nerve is a sensitive physiological structure located in the vicinity of cardiac tissue that may be targeted for one or more treatment applications (such as ablation to treat an arrhythmia, for example). The induced response may then be used to establish or otherwise define a threshold or baseline value. Subsequent activity or physiological changes occurring in the patient during a therapeutic procedure may be compared to the baseline or threshold value and thus generate an alert and/or be used to modify one or more parameters of the delivered treatment. Although the system 10 may be used to stimulate and monitor the phrenic nerve, it will be understood that other areas of non-target tissue and/or anatomical structures, such as other nerves or muscles, may instead be stimulated and monitored to prevent incurring damage to those non-target tissues during the delivery of treatment or ablation energy to an area of target tissue.

Although not shown, the system 10 may include one or more sensors to monitor the operating parameters throughout the system, including for example, pressure, temperature, delivered voltage, or the like, and for measuring and monitoring one or more tissue characteristics, such as ECG waveforms, tissue impedance, or the like, in addition to monitoring, recording or otherwise conveying measurements or conditions within the medical device 12 or the ambient environment at the distal portion of the medical device 12. The sensor(s) may be in communication with the control unit 14 for initiating or triggering one or more alerts or therapeutic delivery modifications during operation of the medical device 12.

Referring now to FIGS. 3-6, contour plots are shown that each illustrates a relationship between voltage, pulse width, and relative distance between the treatment element and an area of non-target tissue, such as the phrenic nerve. These relationships may be used to determine the maximum amount of energy that can be delivered at a particular treatment location and/or from specific electrodes and/or to determine how far from an area of non-target tissue the treatment element (or specific electrodes) must be to avoid damaging the non-target tissue, such as the phrenic nerve. Such data may be stored and accessed by the processing circuitry 46 for the automatic or semi-automatic operation of the system 10. In one embodiment, the processing circuitry 46 may be configured to use such data to determine a maximum stimulation distance from the treatment element based on energy delivery parameters, type of medical device used, number of electrodes, treatment element configuration, or the like, and to determine whether an area of non-target tissue lies within that maximum stimulation distance (and therefore may be adversely affected by the subsequent delivery of treatment and/or ablation energy). The processing circuitry 46 further may be configured to determine recommended energy delivery parameters that would not adversely affect the area of non-target tissue, based at least in part on the distance between the treatment element 16 and the non-target tissue (for example, based at least in part on a relative electrode pair distance).

Figure 2:
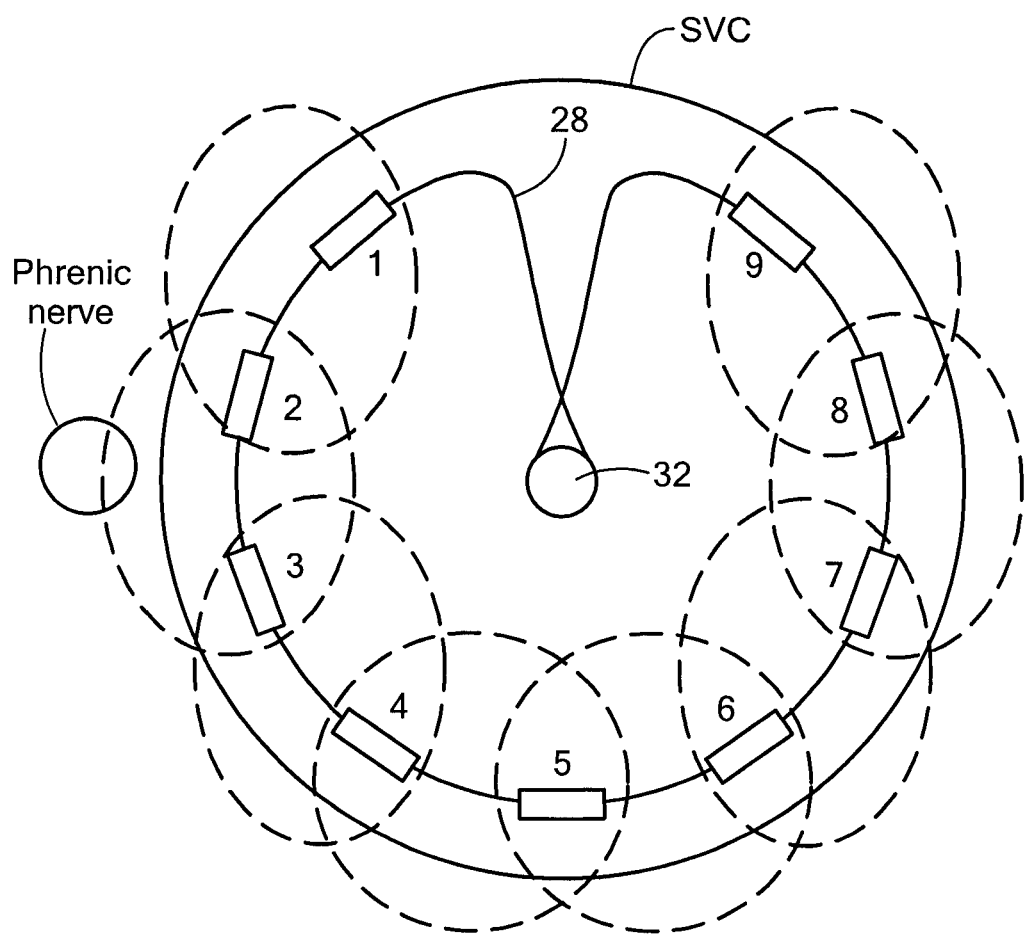
FIG. 2 shows an exemplary placement of a treatment element at a location proximate the phrenic nerve.

To generate the data shown in each of FIGS. 3-6, a device having a treatment element with nine electrodes was oriented within the superior vena cava (SVC) such that Electrodes 2 and 3 were the nearest to the phrenic nerve. In one embodiment, such as that shown in FIG. 2, the treatment element 16 includes nine electrodes, numbered as Electrodes 1-9. When the treatment element 16 is in the first configuration, the space between each successive electrode pair is the same. That is, the space between Electrodes 1 and 2 is the same as the space between Electrodes 2 and 3, which is the same as the space between Electrodes 4 and 5, and so on. When the treatment element 16 is in the second configuration, however, there may be a larger space between Electrodes 1 and 9 as between any other electrode pair. Therefore, for data acquisition purposes, Electrodes 2 and 3 may be positioned closest to the area of non-target tissue to be evaluated (as shown in FIG. 2). FIG. 2 also illustrates exemplary energy fields delivered between electrode pairs, depicted as circles enclosing each electrode pair.

Each tick on the y-axis (0-6) of the contour plots in FIGS. 3-6 represents a successive electrode pair and, therefore, a relative distance from the delivered energy and the anatomical target of interest: tick 0 represents electrode pair 2 and 3; tick 1 represents electrode pair 3 and 4; tick 2 represents electrode pair 4 and 5, tick 3 represents electrode pair 5 and 6; tick 4 represents electrode pair 6 and 7; tick 5 represents electrode pair 7 and 8; and tick 6 represents electrode pair 8 and 9. For the reasons discussed above, data was not collected from electrode pair 9 and 1. Several voltages of energy (10 V, 20 V, 30 V, 40 V, 50 V, 75 V, and 100 V) were delivered from the eight electrode pairs at a particular or predetermined pulse width (a pulse width of 5 µs in FIG. 1, a pulse width of 10 µs in FIG. 2, a pulse width of 25 µs in FIG. 3, and a pulse width of 50 µs in FIG. 4). At each pulse width, voltage, and electrode pair combination, a single biphasic pulse was delivered four times and assessed independently for a stimulation response in the phrenic nerve. The presence of a stimulation response was determined both manually (with a binary yes/no determination) and with one more accelerometers, and data acquired from the two methods were compared to confirm manual observations.

Figure 3:
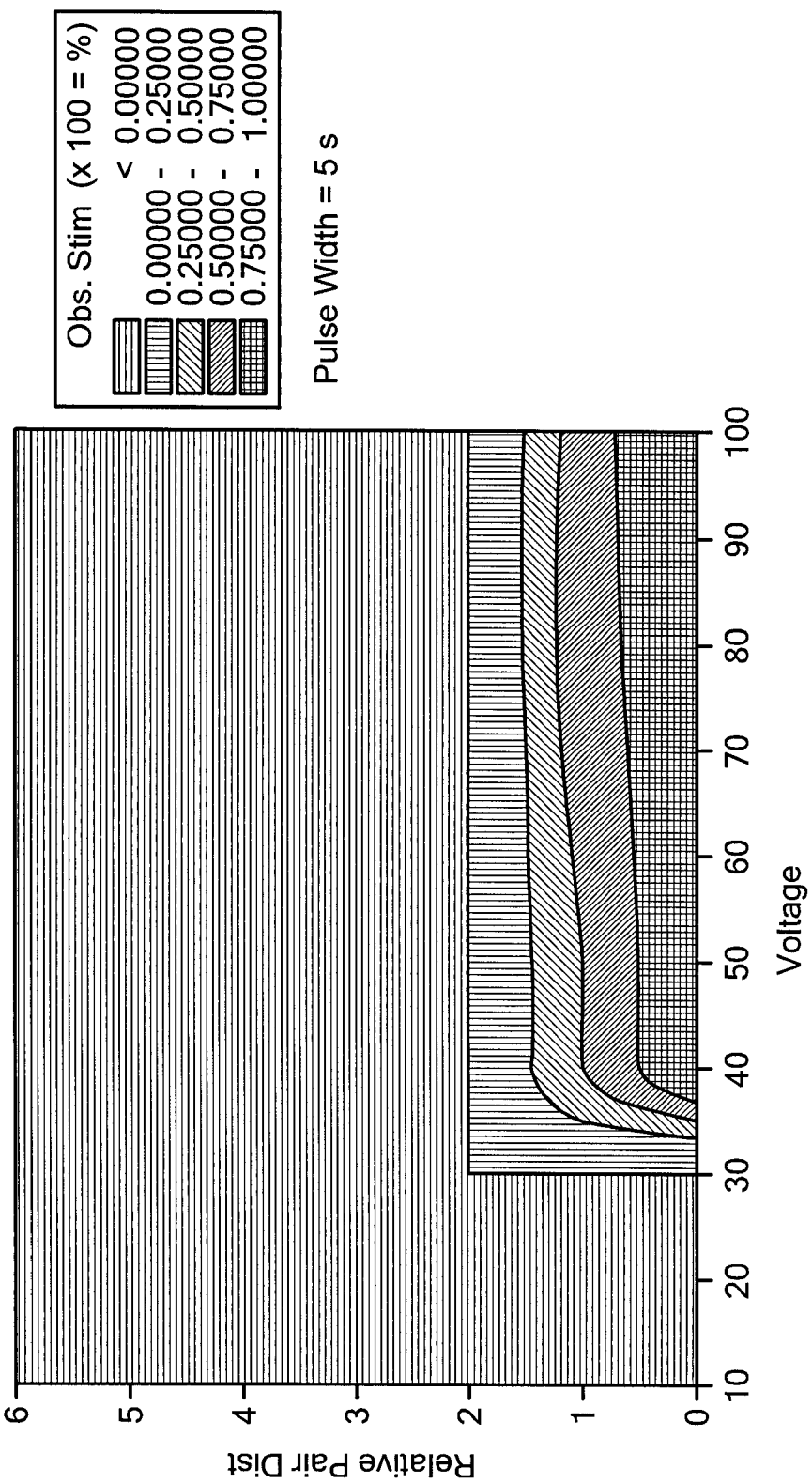
FIGS. 3-6 show contour plots showing exemplary data illustrating relationships between voltage, pulse width, and relative distance between a treatment element and an area of non-target tissue.
Figure 4:
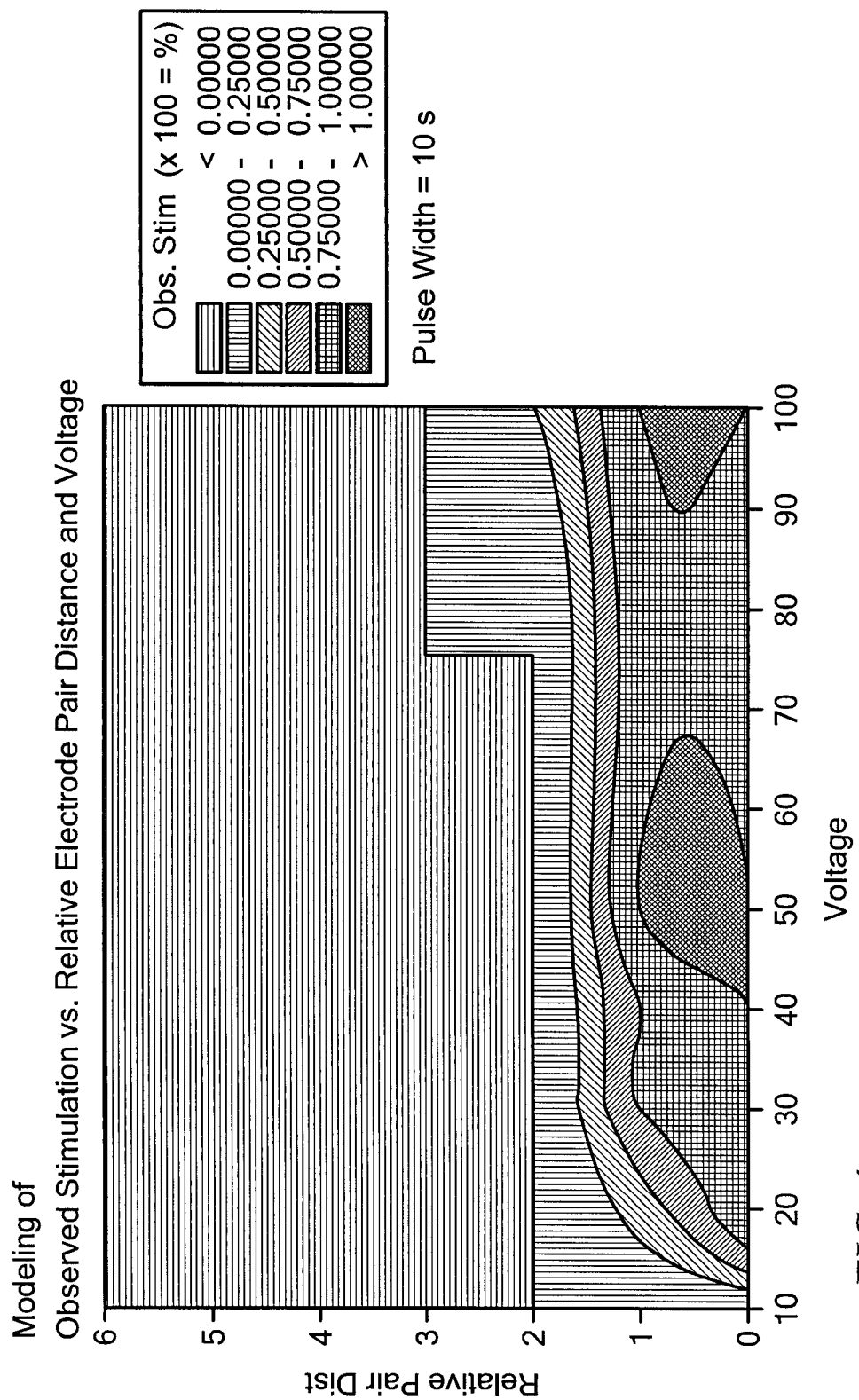
Figure 5:
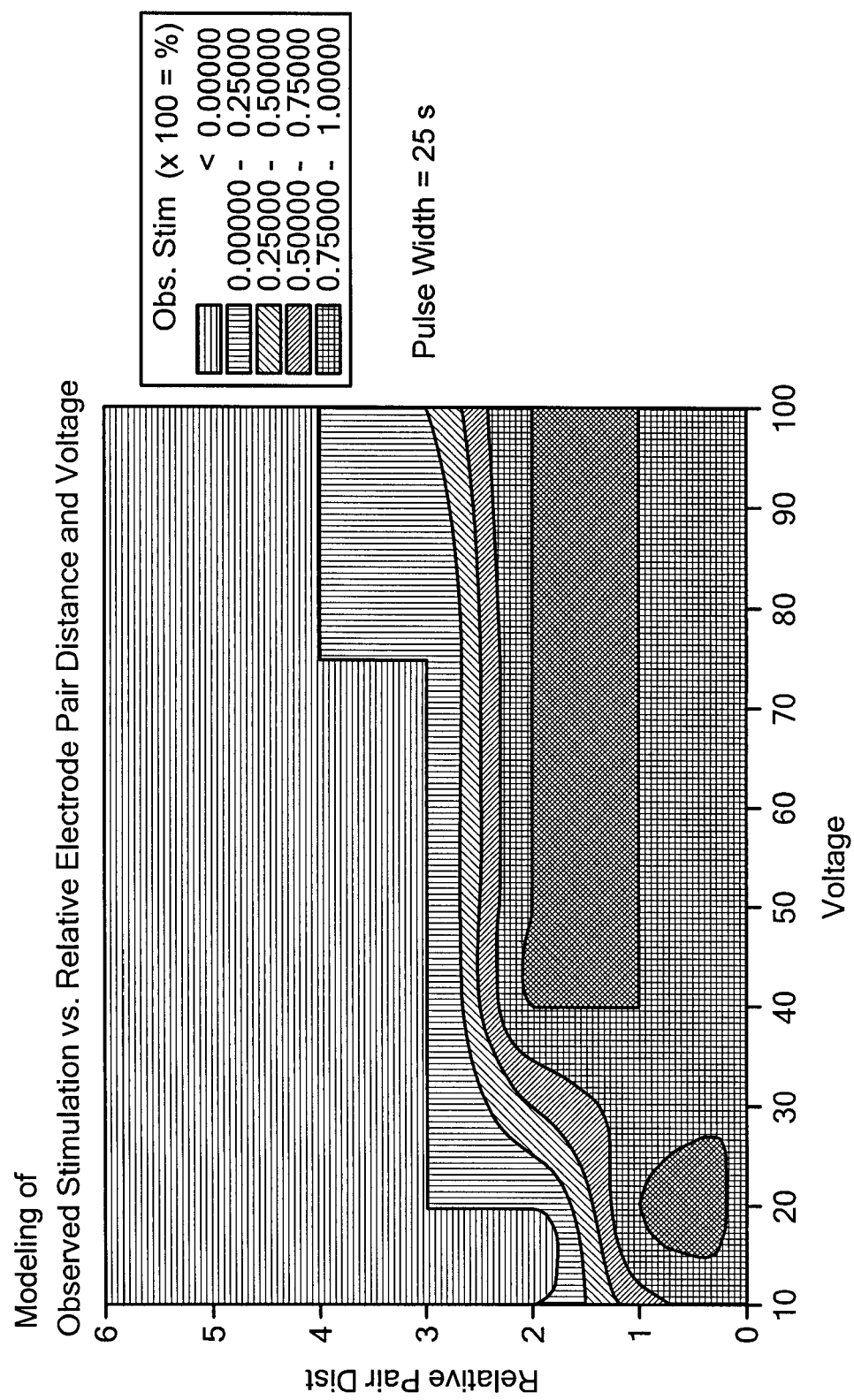
Figure 6:
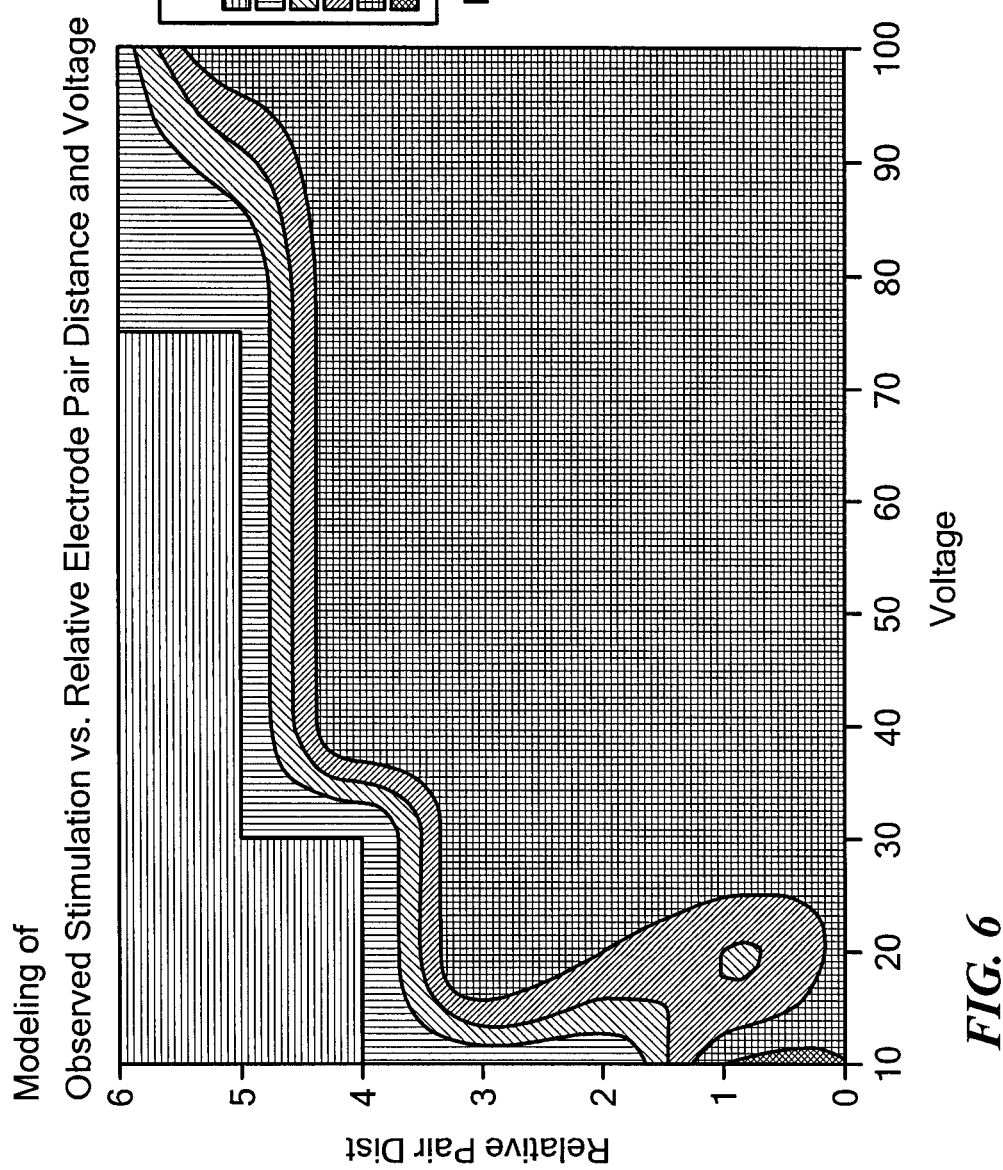
Figure 7:
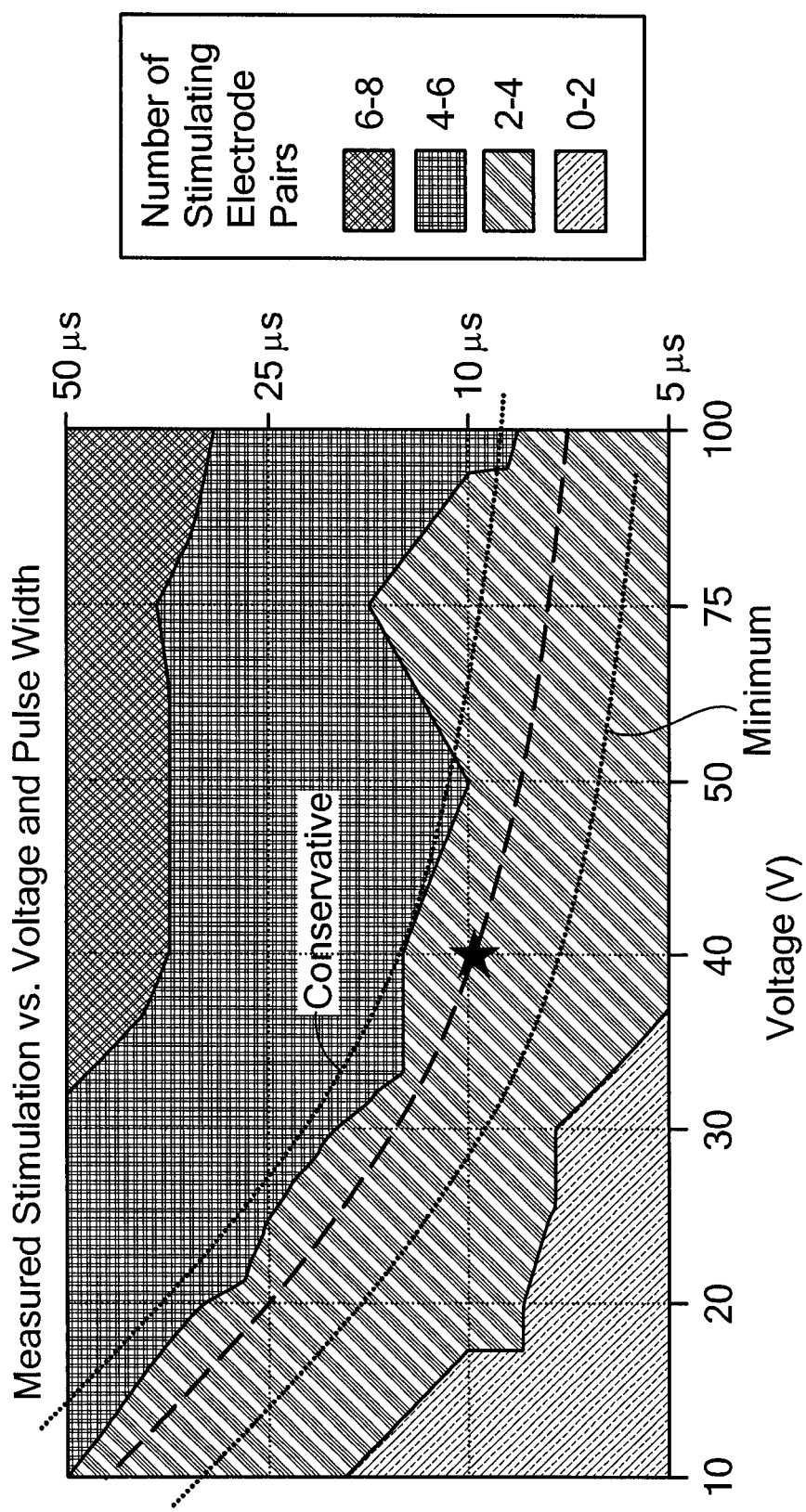
FIG. 7 shows a graphical representation of an effect of voltage and pulse width on stimulation distance from an area of non-target tissue.
Figure 8:
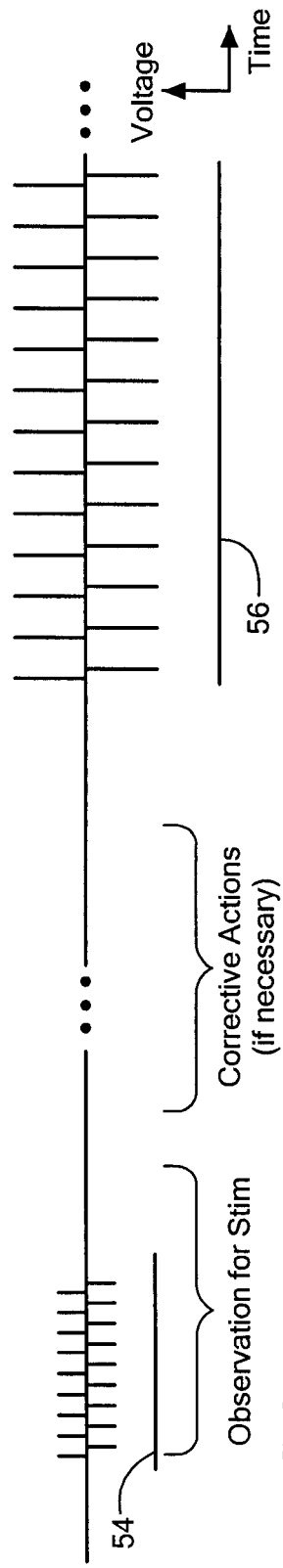
FIG. 8 shows an exemplary waveform for a medical procedure, the waveform including a first embodiment of a low-voltage, pre-treatment pulse routine delivered before an irreversible electroporation routine.
Figure 9:
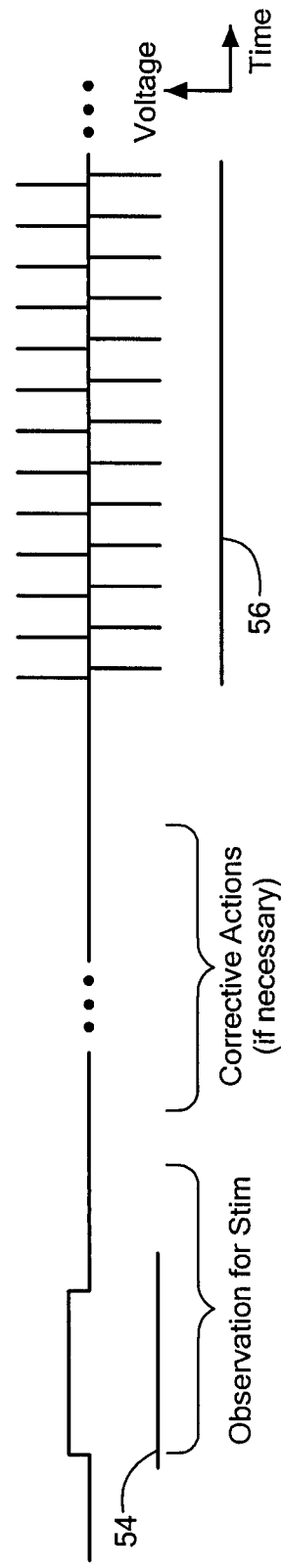
FIG. 9 shows an exemplary waveform for a medical procedure, the waveform including a second embodiment of a low-voltage, pre-treatment pulse routine delivered before an irreversible electroporation routine.
Figure 10:
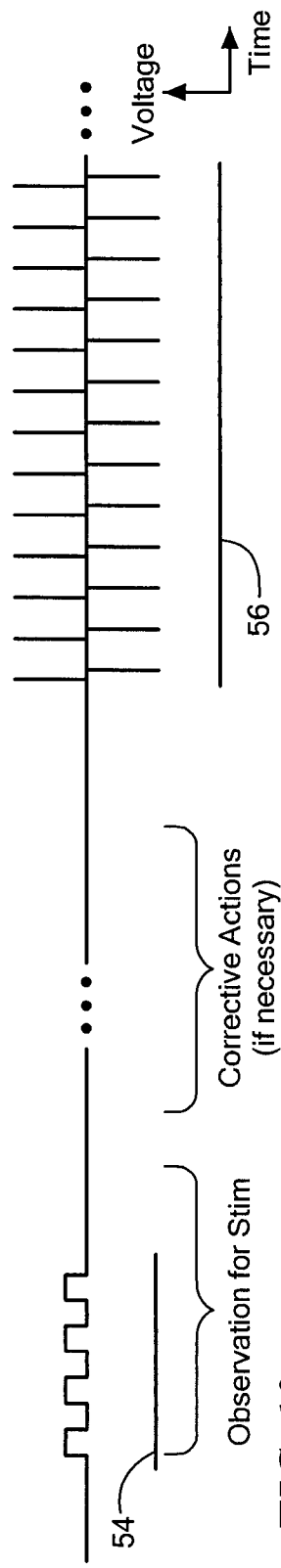
FIG. 10 shows an exemplary waveform for a medical procedure, the waveform including a third embodiment of a low-voltage, pre-treatment pulse routine delivered before an irreversible electroporation routine.
Figure 11:
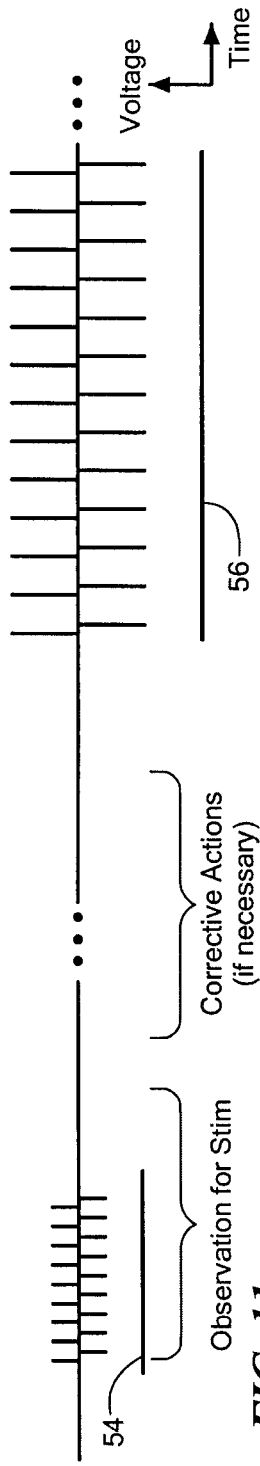
FIG. 11 shows an exemplary waveform for a medical procedure, the waveform including a fourth embodiment of a low-voltage, pre-treatment pulse routine delivered before an irreversible electroporation routine.

FIG. 7 shows a graphical representation of an effect of voltage and pulse width on a stimulation distance from an area of non-target tissue. As the electrode width and spacing between electrodes may be known, these known distances may be used to calculate a distance between electrodes 18 delivering energy and the non-target tissue. For example, at a voltage of 10 V and a pulse width of 5 µs, between zero and two pairs of the eight electrode pairs may have a stimulation effect on an area of non-target tissue, such as the phrenic nerve, when the electrodes 18 are positioned relative to the phrenic nerve as shown in FIG. 2. Conversely, at a voltage of 100 V and a pulse width of 50 µs, between six and eight pairs of the eight electrode pairs may have a stimulation effect on an area of non-target tissue, such as the phrenic nerve, when the electrodes 18 are positioned relative to the phrenic nerve as shown in FIG. 2. The contour plots of FIGS. 3-6 show this data in a different way: for example, FIG. 3 shows that when energy is delivered at a voltage of 10 V at a pulse width of 5 µs, none of the electrode pairs may have a stimulation effect on an area of non-target tissue. It was found that delivering energy at a voltage of 40 V and a pulse width of 10 µs gave a two-electrode-pair stimulation distance from the non-target tissue and was not an overly conservative regime and, therefore, did not give false positives and/or potentially compromise efficacy. Thus, this data may be used to determine whether the application of energy at a particular voltage and/or pulse width will penetrate deeply enough into the area of target tissue to have an effect on (in one embodiment, stimulate), and therefore potentially damage, an area of non-target tissue. Put another way, the processing circuitry 46 may be configured to calculate during the pre-treatment pulse regime, based on the presence or absence of a stimulation response in the non-target tissue, and the magnitude of that stimulation response, how much energy can be safely delivered to the area of target tissue without causing unintended damage to the non-target tissue. However, the depth of energy penetration may be device dependent. As such, the processing circuitry 46 may include data from a number of different devices. The processing circuitry 46 may be configured to recognize and identify any of a number of medical devices, and may apply the correct data for that particular device to accurately evaluate the effect of energy delivery by that device. In one embodiment, the processing circuitry 46 may be configured to access a look-up table based on the given parameters (device, ablation settings, target tissue, and the like). Similarly, a test pulse parameter may be chosen that will effect a stimulation response from farther away, such as may be observed from a relative distance equal to four or five electrode pairs from the phrenic structure. This greater distance may be used if a more aggressive therapy parameter set is desired or a capability of the system such as, for example, a higher voltage applied for electroporation. Some stimulation of non-target tissue may be expected and allowed for a particular treatment of target tissue, as long as the user and/or processing circuitry 46 determines prior to the delivery of treatment/ablation energy that the treatment does not produce or unnecessarily risk adverse effects in the non-target tissue. The pre-treatment pulse routine may enable the user and/or processing circuitry 46 to determine whether a planned treatment would have an adverse effect on the non-target tissue, even if some safe level of stimulation of the non-target tissue is caused.

Referring now to FIGS. 8-11, exemplary waveforms of a low-voltage, pre-treatment pulse routines delivered before an irreversible electroporation routine are shown. In all three examples, the user initiates the pre-treatment pulse routine 54 for a first period of time, observes the non-target tissue for a stimulation effect caused by the pre-treatment pulse routine, takes corrective action (if necessary) if the results of the pre-treatment pulse routine indicate that energy delivery at the selected parameters would cause unintended damage to the non-target tissue, then delivers a treatment or ablation energy routine 56, such as the delivery of energy sufficient to cause irreversible electroporation, for a second period of time. The second period of time may be less than, more than, or the same as the first period of time. In one embodiment, the first period of time (time for the pre-treatment pulse routine 54) may be approximately 25 μs. The low-voltage, pre-treatment pulse routine 54 may include the delivery of energy that is biphasic or monophasic, and bipolar or monopolar. Additionally or alternatively, the low-voltage, pre-treatment pulse routine 54 may include the delivery of energy (for example, one or more pulses of energy) that has one or more other waveforms, such as sinusoidal, triangular, trapezoidal, ramped, irregular, or the like. The pre-treatment pulse routine 54 of FIG. 8 includes the delivery of a plurality of biphasic, low-voltage (between 0.1 V and 100 V) pulses. The pre-treatment pulse routine 54 of FIG. 9 includes the delivery of a single monophasic, low-voltage (between 0.1 V and 100 V) pulse over the first period of time. The pre-treatment pulse routine 54 of FIG. 10 includes the delivery of a plurality of monophasic, low-voltage (between 0.1 V and 100 V) pulses over the first period of time. Finally, the pre-treatment pulse routine 54 of FIG. 11 includes the delivery of a single biphasic, low-voltage (between 0.1 V and 100 V) pulse. In one embodiment, energy is delivered during the pre-treatment pulse routine at a voltage of 40 volts with a pulse width of 10 μs. Energy having these characteristics may be insufficient to cause any damage to the non-target tissue, but may still produce a stimulation effect in the non-target tissue that could be observed by the system 10 and/or the user.

A system 10 such as that discussed herein may include hardware and software to not only deliver a pre-treatment pulse routine quickly and easily, but also to evaluate a patient response to the pre-treatment pulse routine and adjust a planned treatment or ablation energy delivery accordingly. Alternatively, existing ablation systems, such as pulsed-field ablation and/or electroporation systems, may be retrofitted with hardware and/or software discussed herein to add these capabilities. Although irreversible electroporation is discussed herein and shown in the figures, it will be understood that other existing ablation systems may also be retrofitted with hardware and/or software discussed herein, such as RF ablation systems, cryoablation systems, high intensity focused ultrasound (HIFU), or any other energy modality system that can include energy delivery components and electrical connections to the target area through which the pre-treatment pulse routine may be applied. In one embodiment, an existing electroporation system may have processing circuitry that is configured to execute software for delivering energy according to one or more switching and/or timing patterns. This existing system may be retrofitted by modifying the processing circuitry and/or software for delivering energy according to one or more switching and/or timing patterns that result in delivery of the exemplary waveforms discussed herein. Further, in one embodiment, the system 10 includes a user input device 48, or is retrofitted to include a dedicated user input device 48, such as a button, switch, touch screen menu, or the like, that the user can operate to initiate a pre-treatment pulse routine without further input from the user. The processing circuitry 46 may be configured to then determine any effects in the patient (such as phrenic nerve stimulation) caused by the pre-treatment pulse routine and automatically adjust energy delivery and/or system parameters automatically based on that determination and/or communicate that determination to the user. In one embodiment, the processing circuitry 46 may be configured to determine a maximum stimulation distance from the treatment element 16 and may be configured to determine whether an area of non-target tissue lies within the maximum stimulation distance if treatment and/or ablation energy were to be delivered at current delivery parameters (for example, currently set delivery voltage and/or pulse width). Additionally or alternatively, the user may set and/or change energy delivery and/or system parameters based on effects in the patient caused by the pre-treatment pulse routine and/or based on information communicated to the user by the control unit 14. In one embodiment, the processing circuitry 46 may prevent the manual initiation of the delivery of treatment and/or ablation energy by the user if the processing circuitry 46 determines that delivery of the treatment and/or ablation at the currently selected parameters would cause unintended damage to non-target tissue. In one embodiment, the control unit 14 may display or sound one or more visual or audible alerts. The pre-treatment pulse routine may be used before and/or after steps to assess electrode location relative to the target treatment location. Further, the pre-treatment pulse routine may eliminate the need to use electrophysiological (EP) systems to independently check for nerve activation.

Figure 14:
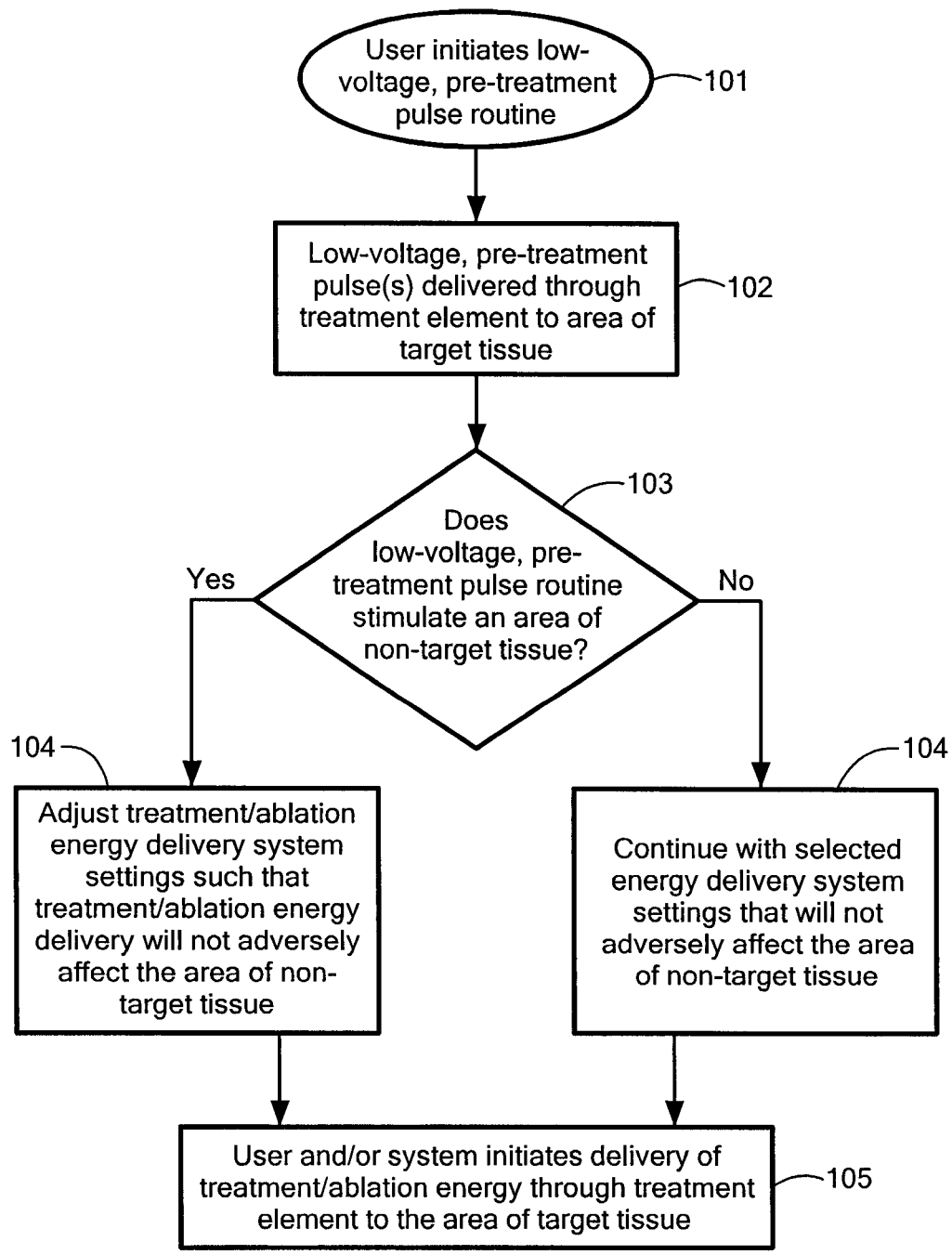
FIG. 14 shows an exemplary method of delivering a low-voltage, pre-treatment pulse routine and treatment or ablation energy.

Now referring to FIG. 14, a method delivering a low-voltage, pre-treatment pulse routine and treatment or ablation energy is shown. In the first step 101, once the treatment element 16 is positioned proximate or in contact with an area of target tissue, the user may initiate delivery of the low-voltage, pre-treatment pulse routine. In one embodiment, the user may manually initiate the pre-treatment pulse routine by interacting with or activating one or more user input devices, such as a button, switch, touchscreen display, or the like. This pre-treatment pulse routine may include monophasic or biphasic waveforms (for example, as shown in FIGS. 8-11), and may be delivered by the energy source 44 through the treatment element 16 in bipolar or monopolar mode (such as in the second step 102). In one embodiment, the treatment element 16 includes nine electrodes 18 (eight electrode pairs) and is transitionable between a linear, or at least substantially linear, first configuration and a hooped, circular, or arcuate, or at least substantially hooped, circular, or arcuate, second configuration (for example, as shown in FIGS. 1 and 2). In one embodiment, the low-voltage, pre-treatment pulse routine energy is delivered at a voltage of 40 V and a pulse width of 10 µs. However, it will be understood that the voltage and/or pulse width of the low-voltage, pre-treatment pulse routine may be selected or adjusted to suit any of a number of variables such as system parameters, medical device used, target tissue type, non-target tissue type, or the like. In one embodiment, data such as those shown in FIGS. 3-7 may be referenced to determine an appropriate pre-treatment pulse routine. The pre-treatment pulse routine may be configured or chosen such that it is capable of having a stimulation effect within an area of non-target tissue when the area of non-target tissue is within a predetermined distance from an area of target tissue, but will not have a stimulation effect within the area of non-target tissue when the area of non-target tissue is outside of the predetermined distance from the area of target tissue.

One or more stimulation monitoring devices 50 (such as one or more accelerometers) may be placed on the patient's skin proximate the diaphragm. The one or more stimulation monitoring devices 50 may transmit signals, through either a wireless or wired connection, to the processing circuitry 46 of the control unit 14. For example, under certain conditions the stimulation monitoring device(s) 50 may record movement of the diaphragm in response to the pre-treatment pulse routine. In the third step 103, the processing circuitry 46 may determine whether the pre-treatment pulse routine has a stimulation effect on an area of non-target tissue, such as the phrenic nerve, based on signals received from the stimulation monitoring device(s) 50. Additionally or alternatively, the user may determine whether the pre-treatment pulse routine has a stimulation effect on an area of non-target tissue, such as the phrenic nerve, based on tactile, visual, or other signals observable by the user (for example, by palpating the patient's body to detect a presence of diaphragmatic contractions). Additionally or alternatively, the control unit 14 may communicate information to the user, such as information or data received from the stimulation monitoring device(s) 50, and the user may determine whether the pre-treatment pulse routine has a stimulation effect on the area of non-target tissue.

In the fourth step 104, the pre-treatment pulse routine is ceased and treatment and/or ablation energy delivery system settings may be adjusted, if necessary, and/or the method may proceed to the treatment and/or ablation energy delivery step. If it is determined in the third step 103 that the low-voltage, pre-treatment pulse routine has a stimulation effect on the area of non-target tissue, the processing circuitry 46 may automatically or semi-automatically, or the user may manually, adjust energy delivery system settings such that the subsequent delivery of treatment and/or ablation energy will not adversely affect the area of non-target tissue. For example, the voltage and/or pulse width may be adjusted or modified before initiation of treatment and/or ablation energy delivery. In one embodiment, the treatment and/or ablation energy delivery may include an irreversible electroporation routine. The pre-treatment pulse routine may be repeated as many times as is desired, or until it is determined by the user and/or the processing circuitry 46 that the position of the treatment element 16 and/or energy delivery system settings are not such that subsequent delivery of treatment energy will have an undesired effect on the area of non-target tissue. Further, the period of no energy delivery immediately following a pre-treatment pulse routine may provide the user with the opportunity to abort the delivery of treatment and/or ablation energy before the delivery of treatment and/or ablation energy is initiated. If it is determined in the third step 103 that the low-voltage, pre-treatment pulse routine does not have a stimulation effect on the area of non-target tissue, it may be unnecessary to adjust or modify treatment and/or ablation energy delivery system settings and the procedure may continue.

Figure 12:
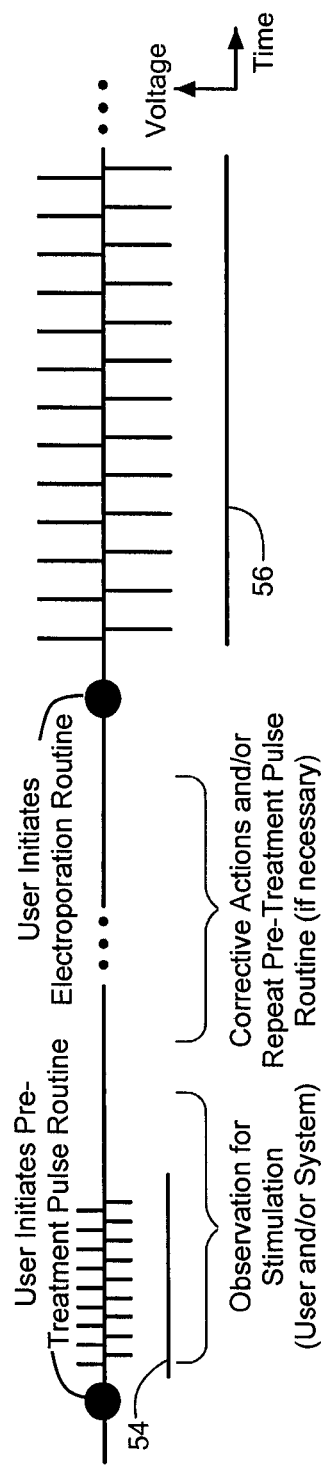
FIG. 12 shows an exemplary timeline for a medical procedure in which a user manually initiates a pre-treatment pulse routine and later manually initiates an irreversible electroporation routine.
Figure 13:
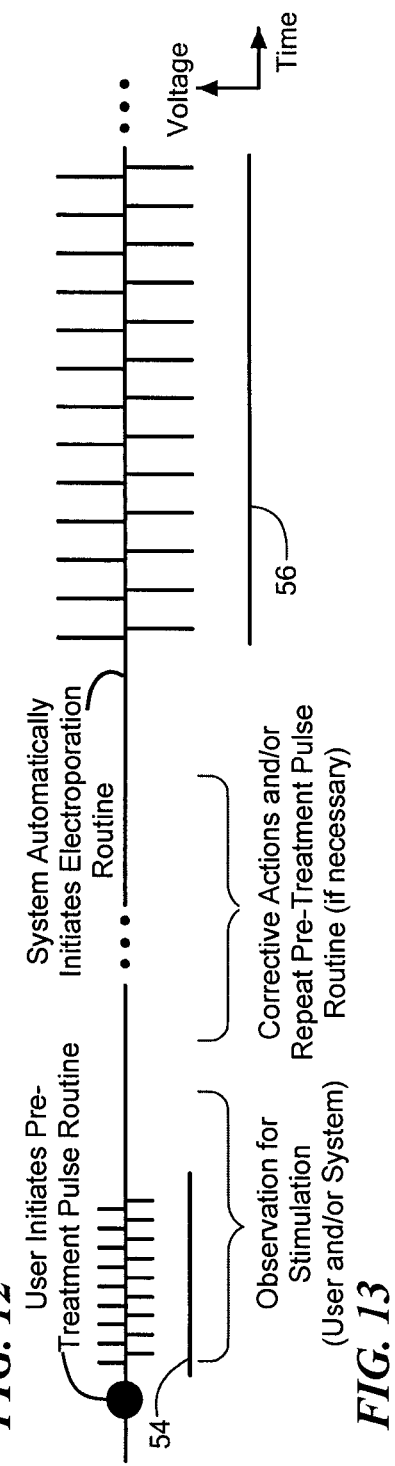
FIG. 13 shows an exemplary timeline for a medical procedure in which a user manually initiates a pre-treatment pulse routine and the medical system automatically initiates an irreversible electroporation pulse routine.

In the fifth step 105, the user and/or the processing circuitry 46 may initiate the delivery of treatment and/or ablation energy, such as irreversible electroporation energy. In the timeline shown in FIG. 12, the user may manually initiate the delivery of the treatment and/or ablation energy by interacting with or activating one or more user input devices, such as a button, switch, touchscreen display, or the like. Alternatively, in the timeline shown in FIG. 13, the processing circuitry 46 may automatically initiate the delivery of the treatment and/or ablation energy without further input or instruction from the user when the processing circuitry 46 determines that (for example, in the third step 103) that the low-voltage, pre-treatment pulse routine does not have a stimulation effect on the area of non-target tissue.

In one embodiment, a medical system 10 includes a medical device 12 having a treatment element 16; and a control unit 14 in communication with the medical device 12, the control unit 14 being configured to: deliver a low-voltage, pre-treatment pulse routine 54 through the treatment element 16 to an area of target tissue, the low-voltage, pre-treatment pulse routine being configured to have a stimulation effect within an area of non-target tissue when the non-target tissue is within a predetermined distance from the area of target tissue and to not have a stimulation effect within the area of non-target tissue when the area of non-target tissue is outside of the predetermined distance from the area of target tissue; and deliver an ablation energy routine 56 through the treatment element 16 to the area of target tissue when the low-voltage pulse routine does not have a stimulation effect on the area of non-target tissue.

In one aspect of the embodiment, delivery of the ablation energy routine 56 includes the use of at least one of irreversible electroporation, radiofrequency ablation, cryoablation, and high intensity focused ultrasound.

In one aspect of the embodiment, the system further includes a stimulation monitoring device 50 in communication with the control unit 14. In one aspect of the embodiment, the stimulation monitoring device 50 includes at last one of an accelerometer and an electromyography device.

In one aspect of the embodiment, the control unit 14 is configured to determine whether the low-voltage pulse routine 54 has a stimulation effect on an area of non-target tissue based on signals received by the control unit 14 from the stimulation monitoring device 50.

In one aspect of the embodiment, the control unit 14 is further configured to configure the low-voltage, pre-treatment pulse routine based on the ablation energy routine and adjust the ablation energy routine when the low-voltage, pre-treatment pulse routine has a stimulation effect on the area of non-target tissue.

In one aspect of the embodiment, the control unit 14 is further configured to automatically adjust at least one of voltage and pulse width of the ablation energy routine before an initiation of the ablation energy routine 56 based on the determination of the maximum stimulation distance from the treatment element 16.

In one aspect of the embodiment, the low-voltage, pre-treatment pulse routine 54 includes the delivery of energy having a voltage between 0.1 V and 100 V. In one aspect of the embodiment, the low-voltage, pre-treatment pulse routine 54 includes the delivery of energy having a voltage of 40 V and a pulse width of 10 µs.

In one aspect of the embodiment, the low-voltage, pre-treatment pulse routine 54 includes the delivery of a monophasic pulse.

In one aspect of the embodiment, the low-voltage, pre-treatment pulse routine 54 includes the delivery of a plurality of monophasic pulses.

In one aspect of the embodiment, the low-voltage, pre-treatment pulse routine 54 includes the delivery of at least one biphasic pulse.

In one aspect of the embodiment, the low-voltage, pre-treatment pulse routine 54 includes the delivery of at least one pulse having a sinusoidal waveform.

In one aspect of the embodiment, the control unit 14 includes a user input device 48 for at least one of a user selection of the low-voltage, pre-treatment pulse routine 54 and a user initiation of the low-voltage, pre-treatment pulse routine 54.

In one aspect of the embodiment, the control unit 14 is further configured to automatically deliver the ablation energy routine through the treatment element 16 to the area of target tissue when the control unit 14 determines that the low-voltage pulse routine 54 does not have a stimulation effect on the area of non-target tissue.

In one aspect of the embodiment, the control unit 14 is further configured to accept a user input for an initiation of the delivery of the ablation energy routine 56 through the plurality treatment element 16 to the area of target tissue when the user determines that the low-voltage, pre-treatment pulse routine 54 does not have a stimulation effect on the area of non-target tissue.

In one embodiment, a medical system 10 includes: a medical device 12 having a treatment element 16 with a plurality of electrodes 18; a stimulation monitoring device 50; and a control unit 14 in communication with the medical device 12 and the stimulation monitoring device 50, the control unit 14 including an ablation energy source 44 and being configured to: determine an ablation energy routine; determine a low-voltage, pre-treatment pulse routine based on the ablation energy routine, the low-voltage, pre-treatment pulse routine including the delivery of energy having a voltage between 0.1 V and 100 V; deliver the low-voltage, pre-treatment pulse routine 54 through the treatment plurality of electrodes 18 to an area of target tissue; determine whether the low-voltage, pre-treatment pulse routine 54 has a stimulation effect on an area of non-target tissue; automatically adjust at least one of voltage and pulse width of the ablation energy routine 56 before an initiation of a delivery of the ablation energy to the area of target tissue based on a determination that the low-voltage, pre-treatment pulse routine 54 has a stimulation effect on the area of non-target tissue; and deliver ablation energy through the plurality of electrodes 18 to the area of target tissue.

In one aspect of the embodiment, the low-voltage, pre-treatment pulse routine 54 includes the delivery of energy having a pulse width of 10 µs.

In one embodiment, a method of irreversibly electroporating an area of target tissue without adversely affecting an area of non-target tissue includes: delivering a low-voltage, pre-treatment pulse routine 54 through a treatment element 16 of a medical device 12 to an area of target tissue, the low-voltage, pre-treatment pulse routine 54 including the delivery of energy having a voltage between 0.1 V and 100 V; determining whether the low-voltage, pre-treatment pulse routine 54 has an adverse effect on an area of non-target tissue; when it is determined that the low-voltage, pre-treatment pulse routine 54 has a stimulation effect on the area of non-target tissue, adjusting at least one ablation parameter of an electroporation energy routine 56 before an initiation of electroporation energy delivery to the area of target tissue such that the electroporation energy delivery to the area of target tissue would not have an adverse effect on the area of non-target tissue; and then delivering electroporation energy through the treatment element 16 to the area of target tissue.

In one aspect of the embodiment, the at least one ablation parameter of the electroporation energy routine 56 includes at least one of voltage, number of pulses, number of applications, and pulse width.

In one aspect of the embodiment, the determining whether the low-voltage, pre-treatment pulse routine 54 has an adverse effect on an area of non-target tissue is based at least in part on signals received from a stimulation monitoring device 50.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A medical system, comprising:
   a medical device having a treatment element with a plurality of electrodes;
   a sensor associated with the medical device; and
   a control unit in communication with the treatment element and the sensor, the sensor being configured to monitor operating parameters of the medical system and output a signal to the control unit, the control unit being configured to:
      deliver a low-voltage, pre-treatment pulse routine through the treatment element to an area of target tissue, the low-voltage, pre-treatment pulse routine including delivery of energy having a voltage of between 0.1 V and 40 V;
      identify at least one of the area of target tissue and an area of non-target tissue;
      determine, based on a magnitude of a stimulation response to the low-voltage, pre-treatment pulse routine in the area of non-target tissue and further based on data specifying a relationship between observed stimulation, voltage, pulse width, and distance between the treatment element and the area of non-target tissue, at least one energy delivery parameter for delivering ablative energy through the treatment element that can safely be delivered to the area of target tissue without adversely affecting the area of non-target tissue; and
      deliver an ablation energy routine through the treatment element to the area of target tissue using the at least one energy delivery parameter; and
   a stimulation monitoring device in communication with the control unit, the stimulation monitoring device including an electromyography device being configured to record diaphragmatic and thoracic measurements.

2. The medical system of claim 1, wherein delivery of the ablation energy routine includes using at least one of irreversible electroporation, radiofrequency ablation, cryoablation, and high intensity focused ultrasound.

3. The medical system of claim 1, wherein the stimulation monitoring device includes an accelerometer.

4. The medical system of claim 1, wherein the control unit is configured to determine whether the low-voltage, pre-treatment pulse routine has a stimulation effect on the area of non-target tissue based on signals received by the control unit from the stimulation monitoring device.

5. The medical system of claim 1, wherein the control unit is further configured to:
select the low-voltage, pre-treatment pulse routine based on the ablation energy routine; and
adjust the ablation energy routine when the low-voltage, pre-treatment pulse routine has a stimulation effect on the area of non-target tissue.

6. The medical system of claim 5, wherein the control unit is further configured to automatically adjust at least one of a voltage and a pulse width of the ablation energy routine before an initiation of the ablation energy routine based on a determination of a maximum stimulation distance from the treatment element.

7. The medical device of claim 1, wherein the low-voltage, pre-treatment pulse routine includes a delivery of energy having a voltage between 0.1 V and 30 V.

8. The medical system of claim 7, wherein the low-voltage, pre-treatment pulse routine includes a delivery of energy having a voltage of 20 V and a pulse width of 10 μs.

9. The medical system of claim 1, wherein the low-voltage, pre-treatment pulse routine includes a delivery of a monophasic pulse.

10. The medical system of claim 1, wherein the low-voltage, pre-treatment pulse routine includes a delivery of a plurality of monophasic pulses.

11. The medical system of claim 1, wherein the low-voltage, pre-treatment pulse routine includes a delivery of at least one biphasic pulse.

12. The medical system of claim 1, wherein the low-voltage, pre-treatment pulse routine includes a delivery of at least one pulse having a sinusoidal waveform.

13. The medical system of claim 1, wherein the control unit includes a user input device for at least one of a user selection of the low-voltage, pre-treatment pulse routine and a user initiation of the low-voltage, pre-treatment pulse routine.

14. The medical system of claim 1, wherein the control unit is further configured to automatically deliver the ablation energy routine through the treatment element to the area of target tissue when the control unit determines that the low-voltage pulse routine does not have a stimulation effect on the area of non-target tissue.

15. The medical system of claim 1, wherein the control unit is further configured to accept a user input for an initiation of the delivery of the ablation energy routine through the treatment element to the area of target tissue when the user determines that the low-voltage, pre-treatment pulse routine does not have a stimulation effect on the area of non-target tissue.

16. The medical system of claim 1, wherein the control unit is further configured to:
recognize and identify a plurality of medical devices;
select from the data a portion thereof corresponding to an identified device; and
determine, based on a respective magnitude of a respective stimulation response to a respective low-voltage, pre-treatment pulse routine in the area of non-target tissue and further based on the portion of the data, a respective energy delivery parameter for delivering ablative energy through a respective treatment element of the identified device.

17. A medical system, comprising:
a medical device having a treatment element with a plurality of electrodes;
a stimulation monitoring device, the stimulation monitoring device including:
an electromyography device being configured to record diaphragmatic and thoracic measurements; and
an accelerometer being configured to detect diaphragmatic movement;
a sensor associated with the medical device; and
a control unit in communication with the treatment element, the stimulation monitoring device and the sensor, the sensor being configured to monitor operating parameters of the medical system and output a signal to the control unit, the control unit including an ablation energy source and being configured to:
determine an ablation energy routine;
determine a low-voltage, pre-treatment pulse routine based on the ablation energy routine, the low-voltage, pre-treatment pulse routine including a delivery of energy having a voltage between 0.1 V and 40 V;
deliver the low-voltage, pre-treatment pulse routine through the plurality of electrodes to an area of target tissue;
determine, based on a magnitude of a stimulation response to the low-voltage, pre-treatment pulse routine in an area of non-target tissue and further based on data specifying a relationship between observed stimulation, voltage, pulse width, and distance between the treatment element and the area of non-target tissue, at least one energy delivery parameter for delivering ablative energy through the treatment element that can safely be delivered to the area of target tissue without adversely affecting the area of non-target tissue; and
deliver ablation energy through the plurality of electrodes to the area of target tissue using the at least one energy delivery parameter.

18. The medical system of claim 17, wherein the low-voltage, pre-treatment pulse routine includes a delivery of energy having a pulse width of 10 μs.

19. The medical system of claim 17, wherein the control unit is further configured to:
recognize and identify a plurality of medical devices;
select from the data a portion thereof corresponding to an identified device; and
determine, based on a respective magnitude of a respective stimulation response to a respective low-voltage, pre-treatment pulse routine in the area of non-target tissue and further based on the portion of the data, a respective energy delivery parameter for delivering ablative energy through a respective treatment element of the identified device.

* * * * *